United States Patent
Knuebel et al.

[11] Patent Number: 5,536,843
[45] Date of Patent: Jul. 16, 1996

[54] SYNTHESIS OF INDOLES BY DEHYDROGENATION OF INDOLINES

[75] Inventors: Georg Knuebel; Roswitha Michel, both of Duesseldorf; David Rose, Hilden, all of Germany

[73] Assignee: Henkel Kommanditgesellschaft auf Aktien, Duesseldorf, Germany

[21] Appl. No.: 284,695

[22] PCT Filed: Feb. 4, 1993

[86] PCT No.: PCT/EP93/00261

§ 371 Date: Aug. 25, 1994

§ 102(e) Date: Aug. 25, 1994

[87] PCT Pub. No.: WO93/16076

PCT Pub. Date: Aug. 19, 1993

[30] Foreign Application Priority Data

Feb. 12, 1992 [DE] Germany .................. 42 04 089.2

[51] Int. Cl.$^6$ .................. C07D 209/04; C07D 209/30
[52] U.S. Cl. .................. 548/469; 548/492
[58] Field of Search .................. 548/469, 492

[56] References Cited

FOREIGN PATENT DOCUMENTS 3737825   5/1988   Germany .

OTHER PUBLICATIONS

Russian Chemical Reviews vol. 36, No. 10, (1967), pp. 753–771 M. N. Preobrashenskaya 'Synthesis of substituted indoles via indolines'.
Bull. Soc. Chim. Fr. (1966), pp. 1335–1342 M. Julia, H. Gaston–Brenton 'Recherches en série indolique. XVII.–Préparation de quelque indolines, indoles et tryptamines oxygénés en position –4 ou –6 par cyclisation "arynique"'.
J. Chem. Soc. (C) (1967) pp. 1424–1427 S. N. Mishra, G. A. Swan 'Studies Related to the Chemistry of Melanins. Part III. Synthesis of 5,6–Dihydroxyindoline' see p. 1427.
Tetrahedron Lett. No. 10, (1970) pp. 723–726 T. Kametani et al. 'A Novel Formation of the Indole Derivatives by Phenolic Oxidative Coupling'.
Biochem vol. 7. No. 5, (1968) pp. 1777–1786 M. Wilchek et al. 'The Nonenzymatic Conversion of Tyrosine into Mono–and Dihydroxyindoles'.
J. Chem. Soc. (1950), pp. 1276–1282 J. Harley–Mason 'The Chemistry of Adrenchrome and its Derivatives'.
B. P. Murphy, T. M. Schultz, J. Org. Chem. 50 (1985) 2790.
J. D. BúLock, J. Harley–Mason, J. Chem. Soc. (1951) 2248.
J. Harley–Mason, J. D. BúLock, Nature 166 (1950) 1036.
K. Wakamatsu, S. Ito, Anal. Biochem. 170 (1988) 335.
P. A. Wehrli, F. Pigott, U. Fischer, A. Kaiser, Helv. Chim. Acta 55 (1972) 3057.
J. Harley–Mason, J. Chem. Soc. (1953) 200.
R. J. S. Beer, K. Clarke, H. E. Khorana, A. Robertson, J. Chem. Soc. (1948) 2223.
H. Burton, J. A. Duffield, P. F. G. Praill, J. Chem. Soc. (1950) 1062.
J. D. Benigni, R. L. Minnis, J. Heterocycl. Chem. 2 (1965) 387.

*Primary Examiner*—Jacqueline Haley
*Attorney, Agent, or Firm*—Wayne C. Jaeschke; John E. Drach; Henry E. Millson, Jr.

[57] ABSTRACT

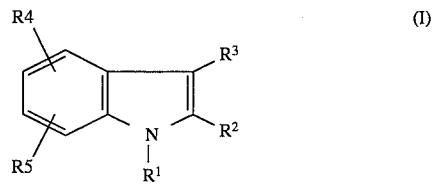

By dehydrating indolines or their salts, the corresponding indoles having formula (I) are obtained. In the formula, $R^1$ and $R^3$ represent independently from each other hydrogen or alkyl groups with 1 to 4 C atoms, $R^2$ stands for hydrogen, a methyl or a carboxyl group, $R^4$ and $R^5$ represent independently from each other hydrogen, amino groups, hydroxy groups, alkyl groups with 1 to 4 C atoms or alkoxy groups with 1 to 4 C atoms, or, in case $R^4$ and $R^5$ are bound to adjacent C atoms, both residues may also represent together an alkylene dioxy group with 1 to 4 C atoms. This process allows high yields of very pure indoles to be produced.

18 Claims, No Drawings

SYNTHESIS OF INDOLES BY DEHYDROGENATION OF INDOLINES

This application is a National Stage application of PCT/EP93/00261 filed Feb. 4, 1993, published as WO93/16076 on Aug. 19, 1993.

BACKGROUND OF THE INVENTION

1. Field of the Invention

This invention relates to a process for the synthesis of indoles by dehydrogenation, preferably catalytic dehydrogenation, of indolines.

2. Statement of Related Art

Indoles are of considerable significance in the fields of pharmacy, cosmetics and dyeing.

The most important process for the synthesis of indole derivatives is Fischer's indole synthesis. In this process, the corresponding indole derivative is formed from the phenyl hydrazone of a keto compound by Diaza-Cope rearrangement and subsequent elimination of ammonia. Unfortunately, this process cannot be universally used and, above all, cannot be used when there are additional substituents at the aromatic 6-ring. The synthesis of 5,6-dihydroxyindoles is particularly difficult because 5,6-dihydroxyindoles are highly sensitive to oxidation on account of their inherent double hydroquinone structure. Their synthesis requires other processes which may be divided into three groups namely:

formation of the 5,6-dihydroxyindole skeleton by reductive cyclization of suitable nitrobenzene precursors (B. P. Murphy, T. M. Schultz, J. Org. Chem. 50 (1985) 2790), formation of the 5,6-dihydroxyindole skeleton by oxidative cyclization of catecholamines (J. D. Bu'Lock, J. Marley-Mason, J. Chem. Soc. (1951) 2248; J. Marley-Mason, J. D. Bu'Lock, Nature 166 (1950) 1036; K. Wakamatsu, S. Ito, Anal. Biochem. 170 (1988) 335; P. A. Wehrli, F. Pigott, U. Fischer, A. Kaiser, Helv. Chim. Acta 55 (1972) 3057 and J. Harley-Mason, J. Chem. Soc. (1953) 200), elimination of 5,6-dihydroxyindoles from 5,6-dialkoxy or 5,6-diacetoxy indoles (R. J. S. Beer, K. Clarke, H. E. Khorana, A. Robertson, J. Chem. Soc. (1948) 2223; H. Burton, J. A. Duffield, P. F. G. Praill, J. Chem. Soc. (1950) 1062; J. D. Benigni, R. L. Minnis, J. Heterocycl. Chem. 2 (1965) 387 and DE-A1-37 37 825).

The disadvantages of these processes lie in the poor yields and complicated purification measures or in complicated syntheses and high prices of the starting materials.

Accordingly, there is a need for a universally usable process for the production of indole derivatives, especially the sensitive 5,6-dihydroxyindole derivatives, in which the products could be obtained in high yields and purity from a readily accessible precursor in a smooth reaction.

It has now surprisingly been found that indoles can readily be obtained by dehydrogenation of the corresponding readily accessible indolines.

DESCRIPTION OF THE INVENTION

Accordingly, the present invention relates to a process for the production of indoles corresponding to general formula I:

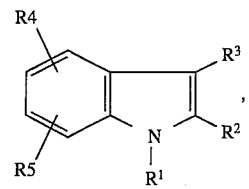

in which $R^1$ and $R^3$ independently of one another represent hydrogen or alkyl groups containing 1 to 4 carbon atoms, $R^2$ represents hydrogen, a methyl group or a carboxyl group, $R^4$ and $R^5$ independently of one another represent hydrogen, amino groups, hydroxy groups, alkyl groups containing 1 to 4 carbon atoms or alkoxy groups containing 1 to 4 carbon atoms or, if they are attached to adjacent carbon atoms, $R^4$ and $R^5$ together may even represent an alkylenedioxy group containing 1 to 4 carbon atoms, by dehydrogenation of indolines corresponding to formula II:

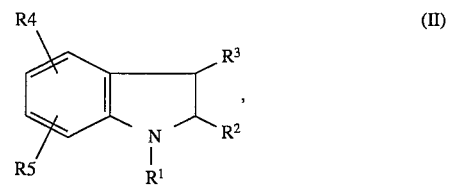

in which $R^1$, $R^2$, $R^3$, $R^4$ and $R^5$ in formula II have the same meaning as in formula I, or salts thereof.

This process may be used with advantage for the production of 5,6-dihydroxyindole derivatives, but especially 5,6-dihydroxyindole itself, which is regarded as a key building block in the biosynthesis of melanin and, accordingly, is also used as a "near-to-nature" starting material for the production of oxidation hair dyes.

The present invention also relates to a process for the production of indoles, $R^4$ and $R^5$ in the indoles of formula I and the indolines of formula II representing hydroxy groups which are preferably attached to carbon atoms 5 and 6 of the indole or indoline skeleton. The parent compound 5,6-dihydroxyindole is preferably produced by this process.

The indolines corresponding to formula II are used either in free form or, if they are capable of salt formation, preferably in the form of their water-soluble organic or inorganic salts, more particularly the hydrobromides or hydrochlorides.

In the context of the invention, the term "dehydrogenation" is merely intended to express the fact that the indole derivatives corresponding to formula I are formed through the loss of 2 hydrogen atoms from the corresponding indoline derivatives corresponding to formula II. Accordingly, the term "dehydrogenation" is not intended to be in any way limiting in regard to the reaction mechanism or the chemical agents to be used for the dehydrogenation according to the invention.

According to the invention, any known oxidizing agents such as, for example, oxygen, sodium borate, hydrogen peroxide and even the agents known for their dehydrogenating effect such as, for example, chloranil, N-bromosuccinimide, sulfur or selenium may be used for this purpose. However, catalytic dehydrogenation is preferred. Any known dehydrogenation catalysts may be used, including for example the oxides of chromium, palladium, molybdenum or zinc. However, nickel-, platinum- or palladium-containing catalysts are preferably used.

Accordingly, the present invention also relates to the process in which the dehydrogenation is carried out in the presence of dehydrogenation catalysts, preferably nickel-, platinum- or palladium-containing catalysts. Catalysts such as these are, for example, fine-particle palladium or platinum on carbon, the noble metal content being between 3 and 10% by weight, or Raney nickel. Palladium on carbon is particularly suitable.

A single dehydrogenation catalyst is preferably used. However, it is also possible in principle to use a mixture of different dehydrogenation catalysts.

Suitable solvents are any of those typically used for catalytic dehydrogenation reactions. However, the dehydrogenation is preferably carried out in water as solvent, above all when 5,6-dihydroxyindoles are to be produced by the process according to the invention. The advantage of using water as solvent is that, in the extraction step following the reaction, the indoles corresponding to formula I, but above all the 5,6-dihydroxyindoles, can be selectively extracted from the aqueous phase without any secondary products using a water-immiscible organic solvent and can thus be obtained in high yields and purity. The pH value of aqueous solution may be between 3 and 11 and is preferably between 4 and 9.

The stoichiometric addition of hydrogen acceptors such as, for example, fumaric acid or maleic acid is of advantage; they are added to the reaction mixture in the form of their water-soluble alkali metal salts.

The following Examples are intended to illustrate the invention without limiting it in any way.

EXAMPLES

Example 1

20 g of 5,6-dihydroxyindoline hydrobromide (86 mmoles) were dissolved in 500 ml of water and 14 g of fumaric acid disodium salt (87 mmoles) and 1.72 g of NaOH (43 mmoles) were successively added to the resulting solution. After addition of 4 g of 5% Pd/C, the reaction mixture was refluxed for 1 hour in an inert gas atmosphere. After filtration, the reaction mixture was continuously extracted for 1 hour with t-butylmethyl ether. After drying of the organic phase over magnesium sulfate and subsequent filtration, the solvent was removed.

9.8 g (66 mmoles) of 5,6-dihydroxyindole were obtained in the form of a light beige-colored powder, corresponding to a yield of 76.5%, based on the 5,6-dihydroxyindoline hydrobromide used. Analysis by HPLC showed that the 5,6-dihydroxyindole thus obtained has a purity of around 98%.

$^1$-NMR (250 MHz, DMSO-$d_6$): 6.12 ppm (d, J=3 Hz, 1H); 6.75 ppm (s, 1H); 6.82 ppm (s, 1H); 6.98 ppm (d, J=3 Hz, 1H); Determination of the coupling constants in MeOH-$d_4$.

Example 2

5 g of 5,6-dihydroxyindoline hydrobromide (22 mmoles) and 860 mg of NaOH (22 mmoles) were dissolved in 500 ml of $H_2O$ and 4.92 g of ammonium peroxodisulfate (22 mmoles) were added to the resulting solution with stirring in an inert gas atmosphere. After stirring for 1 hour at 25° C., the reaction mixture was filtered. It was then continuously extracted with t-butylmethyl ether and the solution obtained was concentrated to dryness.

1.8 g of 5,6-dihydroxyindole were obtained (56% yield, based on 5,6-dihydroxyindoline hydrobromide).

We claim:

1. A process for the production of an indole of formula I

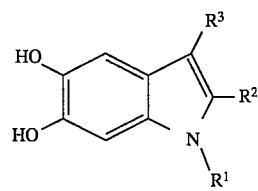

or a salt thereof, wherein each of $R^1$ and $R^3$ is independently hydrogen or an alkyl group having from 1 to 4 carbon atoms and $R^2$ is hydrogen, a methyl group or a carboxyl group, comprising the steps of:

A) dehydrogenating an indoline of formula II or a salt thereof

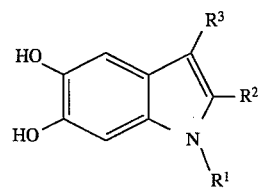

wherein $R^1$ through $R^3$ are defined as above; and

B) isolating the indole of formula I from the resulting reaction mixture.

2. The process of claim 1 wherein said indole of formula I is 5,6-dihydroxyindole.

3. The process of claim 1 wherein step A is carried out in the presence of a dehydrogenation catalyst.

4. The process of claim 3 wherein said dehydrogenation catalyst contains nickel, palladium, or platinum.

5. The process of claim 4 wherein said dehydrogenation catalyst is palladium on carbon, platinum on carbon, or Raney nickel.

6. The process of claim 5 wherein said dehydrogenation catalyst is palladium on carbon.

7. The process of claim 3 wherein the dehydrogenation catalyst is an oxide of chromium, palladium, molybdenum, or zinc.

8. The process of claim 1 wherein step A) is carried out in the presence of a solvent.

9. The process of claim 8 wherein said solvent is water.

10. The process of claim 1 wherein step A) is carried out in the presence of a hydrogen acceptor.

11. A process for the production of an indole of formula I

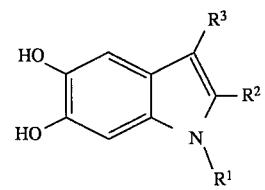

or a salt thereof, wherein each of $R^1$ and $R^3$ is independently hydrogen or an alkyl group having from 1 to 4 carbon atoms and $R^2$ is hydrogen, a methyl group or a carboxyl group, comprising the steps of:

A) dehydrogenating an indoline of formula II or a salt thereof

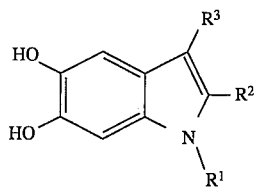

wherein $R^1$ through $R^3$ are defined as above in the presence of water as a solvent;

B) selectively extracting the indole of formula I or its salt from the aqueous reaction mixture resulting from step A) using a water-immiscible organic solvent; and C) isolating the indole of formula I or its salt from the organic solvent.

12. The process of claim 11 wherein in step A) a hydrogen acceptor is also present in the form of a water-soluble alkali metal salt.

13. The process of claim 12 wherein the hydrogen acceptor is a salt of fumaric acid or maleic acid.

14. The process of claim 11 wherein step A) is carried out in the presence of a dehydrogenation catalyst.

15. The process of claim 14 wherein said dehydrogenation catalyst contains nickel, palladium, or platinum.

16. The process of claim 15 wherein said dehydrogenation catalyst is palladium on carbon, platinum on carbon, or Raney nickel.

17. The process of claim 16 wherein said dehydrogenation catalyst is palladium on carbon.

18. The process of claim 11 wherein the indoline of formula II is 5,6-dihydroxyindoline.

* * * * *